(12) United States Patent
Limacher et al.

(10) Patent No.: US 9,066,693 B2
(45) Date of Patent: Jun. 30, 2015

(54) DEVICE FOR MEASURING THE BLOOD FLOW OF A BODY TISSUE

(75) Inventors: Kuno Limacher, Steinhausen (CH); Jérôme Bernhard, Zürich (CH); Jörg Hummen, Kilchberg (CH); Jevgenij Mannhart, Cham (CH); Claudio Steiner, Schwyz (CH)

(73) Assignee: CARAG AG, Baar (CH)

( * ) Notice: Subject to any disclaimer, the term of this patent is extended or adjusted under 35 U.S.C. 154(b) by 312 days.

(21) Appl. No.: 13/057,579

(22) PCT Filed: Jul. 7, 2009

(86) PCT No.: PCT/CH2009/000241
§ 371 (c)(1),
(2), (4) Date: Feb. 8, 2011

(87) PCT Pub. No.: WO2010/015094
PCT Pub. Date: Feb. 11, 2010

(65) Prior Publication Data
US 2011/0137186 A1  Jun. 9, 2011

(30) Foreign Application Priority Data
Aug. 6, 2008 (CH) ........................ 1229/08

(51) Int. Cl.
*A61B 5/02* (2006.01)
*A61B 5/1459* (2006.01)
(Continued)

(52) U.S. Cl.
CPC ............... *A61B 5/1459* (2013.01); *A61B 5/026* (2013.01); *A61B 5/0261* (2013.01); *A61B 5/14553* (2013.01); *A61M 25/0069* (2013.01); *A61M 25/007* (2013.01)

(58) Field of Classification Search
CPC .............................. A61B 5/026; A61B 5/0215
USPC .................................. 600/324, 325, 504, 505
See application file for complete search history.

(56) References Cited

U.S. PATENT DOCUMENTS 5,531,673 A   7/1996   Helenowski
5,579,774 A   12/1996  Miller et al.
(Continued)

FOREIGN PATENT DOCUMENTS

CH   697482    11/2008
EP   1149604   10/2001
(Continued)

OTHER PUBLICATIONS

International Search Report for corresponding International App. No. PCT/CH2009/000241, mailed Apr. 19, 2010.

*Primary Examiner* — Etsub Berhanu
(74) *Attorney, Agent, or Firm* — McDonnell Boehnen Hulbert & Berghoff LLP

(57) ABSTRACT

A device for measuring the blood flow of a body tissue comprises a catheter having a catheter head for the insertion into the inside of a body tissue and a center piece having a light emission surface, out of which an optical conductor leads, and having a reflection surface, which is disposed opposite of the light emission surface and oriented obliquely to the longitudinal axis of the optical conductor. The optical conductor is disposed such that an emitted light beam is directed at the reflection surface, the emitted light beam can be deflected at the reflection surface and reflected into the body tissue, and a reflected light beam can be reflected out of the body tissue at the reflection surface and fed into the optical conductor. The catheter head is divided into an insertion region and a connecting region, wherein the insertion region comprises a plurality of recesses on the surface thereof. In the direction of the connecting region, the insertion region has an increasing diameter. The recesses are provided in the insertion region such that webs are formed in the direction of the connecting region between the recesses along the surface of the catheter head.

17 Claims, 13 Drawing Sheets

(51) Int. Cl.
*A61B 5/026* (2006.01)
*A61B 5/1455* (2006.01)
*A61M 25/00* (2006.01)

(56) References Cited

U.S. PATENT DOCUMENTS

| | | |
|---|---|---|
| 5,643,226 A | 7/1997 | Cosgrove et al. |
| 6,007,478 A | 12/1999 | Siess et al. |
| 6,198,952 B1 * | 3/2001 | Miesel .................. 600/339 |
| 6,572,643 B1 * | 6/2003 | Gharibadeh ................ 623/1.11 |
| 6,625,495 B1 * | 9/2003 | Alon et al. ................... 607/116 |
| 6,697,667 B1 | 2/2004 | Lee et al. |
| 6,749,623 B1 * | 6/2004 | Hsi et al. ......................... 607/88 |
| 7,532,920 B1 * | 5/2009 | Ainsworth et al. .......... 600/342 |
| 2004/0111016 A1 | 6/2004 | Casscells et al. |
| 2005/0043600 A1 * | 2/2005 | Diab et al. .................... 600/344 |
| 2005/0049455 A1 | 3/2005 | Ootawara et al. |
| 2006/0079813 A1 | 4/2006 | Schlumpf |
| 2006/0253007 A1 | 11/2006 | Cheng et al. |
| 2008/0004511 A1 | 1/2008 | Rubinstein et al. |

FOREIGN PATENT DOCUMENTS

| | | |
|---|---|---|
| EP | 1464276 | 10/2004 |
| EP | 1504715 | 2/2005 |

* cited by examiner

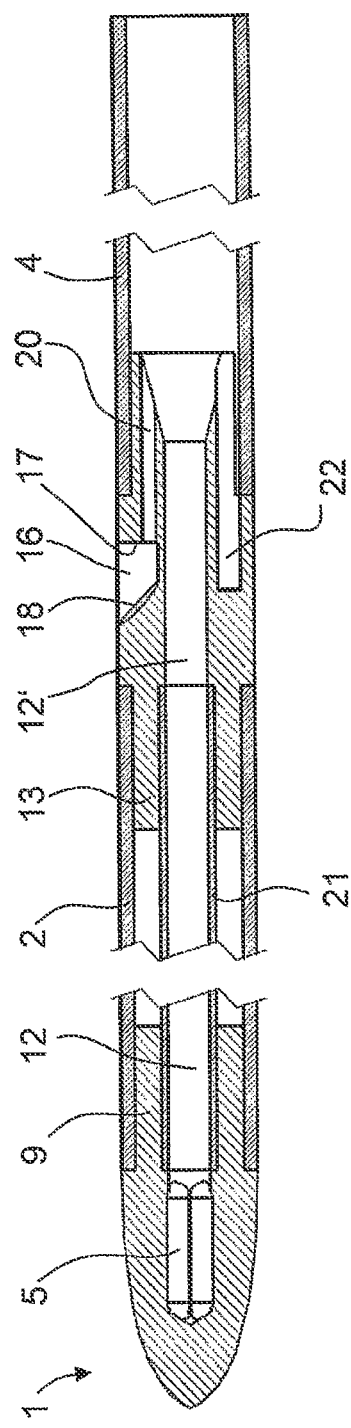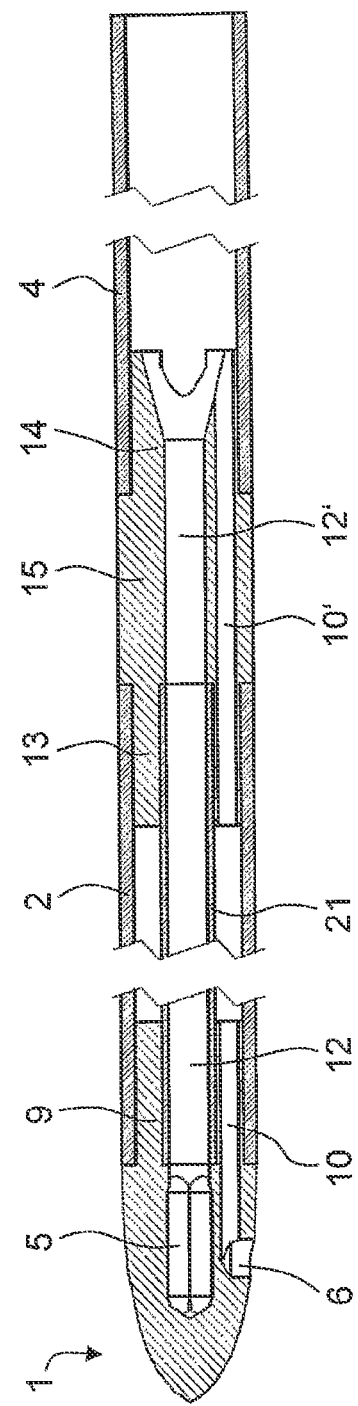
FIG. 6a
FIG. 6b

DEVICE FOR MEASURING THE BLOOD FLOW OF A BODY TISSUE

CROSS REFERENCE TO RELATED APPLICATIONS

The present application is a U.S. National Phase Application pursuant to 35 U.S.C. §371 of International Application No. PCT/CH2009/000241 filed Jul. 7, 2009, which claims priority to Swiss Patent Application No. 1229/08 filed on Aug. 6, 2008. The entire disclosure content of these applications are herewith incorporated by reference into the present application.

FIELD OF THE INVENTION

The present invention relates to a catheter, a catheter head and a device for measuring the flow of blood through a body tissue, particularly through a cerebral tissue. The invention furthermore relates to a catheter, a catheter head and a device for cerebral diagnostics and/or therapy.

BACKGROUND

Various devices for measuring the flow of blood through a body tissue are known from the prior art. To measure the flow of blood through the cerebral tissue of the brain, catheter-type measurement devices are used which carry measurement sensors at their catheter tip. Such catheter probes are inserted into the cerebral tissue though an opening made in the cranium, in order to carry out a measurement of the flow of blood through the tissue. A number of measurement methods are known for this purpose, for example thermal diffusion, ultrasound methods, and near-infrared spectroscopy in association with an indicator.

For example, EP 1 464 276 A1 discloses a measurement device for determining the flow of blood, in which device two octodes are placed on the surface of the head at a distance from each other. One of the octodes is connected to a radiation source which emits radiation with a near-infrared wavelength. Some of the radiation reflected on the cerebral tissue strikes the second octode, such that the intensity can be determined by an evaluation unit. Indocyanine green is used as the indicator, and a beam of light at a wavelength of between 780 and 910 nm is used. In this method of performing a near-infrared spectroscopy measurement, account must be taken of a large number of external influences that have a disadvantageous impact on the measurement of the flow of blood. The beam of light cannot be conveyed directly to the tissue that is to be measured, and instead it first has to pass through the skin, the skull cap, the dura mater, etc., in order to reach the tissue that is to be examined. As a result, the measurement signal is weakened and distorted by absorption and scattering, for example. It is therefore only possible to measure areas of tissue near to the surface of the head. Areas in the interior of the brain, for example near the floor of the ventricle, can be examined only with inadequate precision by this method.

EP 1 504 715 discloses a catheter with a light-emitting optical conductor and a light-receiving optical conductor, the ends of which optical conductors are arranged at a predetermined distance from each other.

Another device for measuring the flow of blood within the cranium is known from U.S. Pat. No. 5,579,774, for example. A catheter probe, inserted into the interior of the brain, comprises a measurement sensor for carrying out laser Doppler flowmetry. The beam of light of a helium-neon laser at 632.8 nm is guided in the axial direction via a light conductor to the measurement area, which lies distally in a continuation of the probe. Some of the incident light is absorbed and reflected by the surrounding tissue and some by the circulating blood. The reflected light is guided through at least one optical fibre to a processing unit. The light reflected from the moving red blood cells undergoes a Doppler shift, from which it is possible to determine the flow rate. The head of the catheter probe has a rounded tip whose diameter widens conically in the distal direction. The blunt tip is pushed through the opening in the cranium and through the subjacent tissue as far as the measurement area lying within the brain. The whole surface of the blunt tip presses against the cerebral tissue and exerts a pressure that can leave behind permanent damage in the brain.

SUMMARY

It is an object of the present invention to make available a device which measures the flow of blood through a body tissue, in particular through deep-lying cerebral tissue, and which is easy and inexpensive to produce and does not distort the measurement.

It is a further object of the invention to make available a device which measures the flow of blood through a body tissue, in particular through deep-lying cerebral tissue, and which has the narrowest possible configuration and permits insertion of the device with minimal trauma, i.e. with minimal injury, into cerebral tissue.

It is a further object of the invention to make available a device which measures the flow of blood through a body tissue, in particular through deep-lying cerebral tissue, and which permits insertion of the measurement device with minimal trauma into cerebral tissue.

It is a further object of the invention to make available a device which measures the flow of blood through a body tissue, in particular through deep-lying cerebral tissue, and which permits reliable measurement of the flow of blood.

It is a further object of the invention to make available a device which measures the flow of blood through a body tissue, in particular through deep-lying cerebral tissue, and which is transportable along with a patient.

In a preferred embodiment of the catheter according to the invention, a single optical fibre is present as optical conductor for the light to be emitted and for the reflected light, and a photodetector and a drainage channel for drainage are present.

In another preferred embodiment of the catheter according to the invention, a single optical fibre is present as optical conductor for the light to be emitted, as are a photodetector in the catheter for the reflected light, and a drainage channel for drainage.

In another preferred embodiment of the catheter according to the invention, the above-described head part is present, as are a pressure sensor and a drainage channel for drainage.

The drainage channel can additionally or alternatively be used as a guide channel. In a catheter made of a largely flexible material, a stiff wire can be pulled through the guide channel, making it easier to insert the catheter into the body tissue.

A preferred embodiment of the invention is a device for measuring the flow of blood through a body tissue comprises a catheter with a catheter head for insertion into the interior of a body tissue, an optical conductor inside the catheter, a light source for emitting a beam of light into the body tissue by means of the optical conductor, and a processing unit for determining the rate of blood flow by means of a beam of light reflected from the body tissue. According to the invention, the catheter has a middle piece with a recess, a cut out, an aperture or an indentation which is oriented inwards into the middle piece and is provided laterally with respect to the longitudinal axis of the catheter. The recess or the like can have a round, oval or parabola-shaped inner surface or, in the case of an indentation for example, can be made up of a plurality of walls. According to the invention, the recess or the like has a surface area from which the optical conductor opens out and from which the beam of light thus emerges, and a further surface area which lies opposite the surface area from which the optical conductor opens out and which is oriented at least partially obliquely with respect to the axis of the optical conductor and preferably also obliquely with respect to the longitudinal axis of the catheter. For simplicity, the two surface areas are referred to hereinbelow as the light exit surface or light exit surface area and as the reflection surface or reflection surface area. The optical conductor emerges from the light exit surface in such a way that the beam of light emitted from the light source is directed to the reflection surface and is deflected by the latter into the surrounding body tissue. The beam of light is absorbed and reflected in the body tissue in a manner characteristic of the flow of blood, as a result of which a reflection light beam is formed which is reflected on the reflection surface and coupled into the optical conductor. The reflection light beam is preferably focussed on the reflection surface. The reflection light beam is transmitted through the optical conductor to the processing unit, where the rate of blood flow can be determined from this delivered signal by comparison with the input signal according to the emitted beam of light.

The catheter thus forms a probe or catheter probe for measuring the flow of blood through the body tissue. The catheter has a specially designed catheter head, as is explained further below, as a result of which it is especially suitable for measurements on cerebral tissue, particularly on deep-lying cerebral tissue. The optical conductor can be formed, for example, by a fibre-optic cable or another light conductor, which is routed through the catheter to the middle piece and to the light exit surface of the latter. The reflection surface can itself have a surface roughness that is of sufficient quality, preferably of mirror-like quality, to allow it to reflect the beam of light from the light conductor. Preferably, a reflector, for example a mirror, is arranged on the oblique surface so as to reflect the beam of light into the surrounding body tissue. It is also advantageous if the reflection surface area has a curved shape in order, on the one hand, to reflect the incident beam of light into the tissue in a focussed manner and, on the other hand, to ensure that the light reflected on the tissue is fed into the optical conductor. In the configuration of the recess with its associated surface areas, the distance between the exit point of the emitted beam of light from the optical conductor and the opposite reflection surface is known and is provided such that the optical conductor focuses the emitted beam on the focal point of the reflection surface if the latter has a curved shape. The emitted beam of light is preferably reflected at an angle of 45° into the surrounding tissue. However, other angles of reflection are also conceivable, e.g. in a range of 30°-60°.

The recess is preferably filled or sealed or plugged with a material transparent to light. The outer surface of the filler material is preferably flush with the circumferential surface of the surrounding area, such that a smooth transition is obtained. Epoxy resin, for example, can be used as filler material. By filling the recess, it is possible to avoid air inclusions in the beam path.

It is preferable to use a light source with coherent light, e.g. a laser or a laser diode, which can emit light in the near infrared range between 780 and 910 nm. Light in this wavelength range is able to penetrate biological tissue. It is preferable to specifically use wavelengths that are suitable for a chosen measurement technique. Light with wavelengths of 785 nm, 850 nm and 905 nm is preferably used, which in particular is absorbed and reflected by oxygenated and deoxygenated hemoglobin and the marker substance indocyanine green. It is also advantageous to use a pulsed light beam or pulsed light beams of variable frequency. The parts of the incident beam of light reflected on the tissue are transformed in the processing unit by means of an analog-digital converter into a meaningful signal relating to the time profile of the presence of oxygenated and deoxygenated blood and of the marker substance.

It is also possible, however, to use a light source that emits light over a broad wavelength spectrum, for example a source of white light. The relevant wavelength ranges for measurement of the flow of blood can then be detected by a spectrometer. However, sources of coherent light have the advantage of requiring less energy.

The catheter probe is also suitable for tissue areas lying far within the brain. For this purpose, the distance between the catheter head and the middle piece is advantageously variable. A connection element, e.g. in the form of a tube, of greater or lesser length can be used depending on the desired measurement range or the desired depth of penetration into the brain. The catheter head can be inserted into the brain as far as the ventricle floor, for example, which then serves inter alia as a reference point for locating the middle piece. The measurement of the flow of blood can thus be performed directly in situ in the areas of body tissue that are of interest.

The device for measuring the flow of blood through a body tissue according to the invention also preferably comprises a holder which is placed on the surface of the head, over an insertion opening in the cranium, and which holds the catheter probe in a predetermined position. The holder has, for example, a contact surface for placing onto the surface of the head and, protruding from the contact surface, a guide tube for the catheter. The holder can avoid penetration of infectious substances into the brain during a measurement. It acts as a barrier against pathogens and contaminants. The guide tube is preferably arranged perpendicularly on the contact surface, such that it guides the catheter head perpendicularly through the cranium and then holds the catheter head perpendicularly in position. In this position, the catheter probe can be turned about its axis without being deflected from its position and damaging surrounding tissue. By turning the probe, the attainable measurement field is greatly enlarged. A measurement can be performed in a 360° sector around the middle piece of the catheter probe.

The catheter probe can also have at least one X-ray marker, which can indicate the position and orientation of the probe in the tissue when an X-ray measurement is being carried out.

If the catheter head and the middle piece are made of metal, their position can be monitored by X-ray methods. In principle, however, other biocompatible materials are also conceivable, in which case the monitoring by X-ray methods can be achieved by opal additives, by electronic components already used in the catheter, or by markers. Moreover, the catheter can be provided with a scale for the depth of penetration into the body tissue and also with an angle scale for indicating the angle position of the middle piece. These features permit a precise locating of the measurement area in the brain.

At the same time, the catheter probe can be equipped with additional measurement sensors. For example, a temperature measurement sensor, e.g. a thermistor or a thermocoupler, can be provided in the middle piece. The temperature sensor can be arranged in an outer area of the middle piece, e.g. in a channel. Since metal has an excellent heat conduction coefficient, it is possible, at the same time as measuring the flow of blood through the tissue surrounding the middle piece, to also detect the temperature of the tissue. Contact with the tissue is not necessary in this case. However, if the middle piece is made of plastic, contact between the measurement sensor and tissue must be ensured. The leads needed for the measurement can be routed through the catheter to the processing unit, in which the temperature signal is received and converted. However, it is also possible to arrange a temperature measurement sensor in a tube area between the tip of the probe and the middle piece.

Moreover, the catheter head and the middle piece of the catheter can be provided with a passage or a drainage channel that permits drainage of the surrounding tissue through the catheter. For this purpose, the catheter head, for example, has at least one opening which leads to the surrounding tissue and which is connected to the drainage channel, such that fluid can be aspirated from the tissue through the channel. Arranged near the drainage opening, there is preferably at least one pressure sensor which is designed, on the one hand, to determine the pressure in the surrounding tissue and, on the other hand, to determine the pressure in the drainage channel. In the event of an occlusion and a subsequent change of pressure in the drainage channel, a signal can be output to the processing unit, such that an alarm can be triggered. In principle, it is also possible to deliver liquid to the tissue by way of the drainage opening, i.e. to inject liquid.

According to a further aspect of the present invention, a catheter head for insertion into a body tissue is provided which is divided into an insertion area and an adjoining connection area. The insertion area comprises several apertures in its surface. Moreover, the insertion area has a diameter that increases in the direction of the connection area. The apertures are provided in the insertion area in such a way that webs extending in the direction of the connection area are formed between the apertures along the surface of the catheter head. The webs begin in an area of the insertion area with a small diameter and end in an area with a greater diameter.

This inventive design of the catheter head permits gentle and largely atraumatic insertion of the catheter head into and through the body tissue, particularly a cerebral tissue. During insertion of the catheter head, the tissue is initially spread apart only by the frontmost area and by the surface of the webs. The tissue is not yet stressed in the area of the apertures between the webs. After the initial spreading, the catheter head is inserted further and the tissue areas at the apertures are also widened by the circumferential surface of the connection area. In this procedure, only minimal direct pressure is applied to the tissue.

The connection area of the catheter head is preferably circular or oval and has a uniform diameter. The diameter is preferably at most 3 mm. The insertion area is closed at the frontmost area of the tip and, for example, is parabola-shaped, round, or in the form of a truncated cone. The apertures can extend in an elongate shape from the insertion area to the connection area. Because of the increasing diameter of the insertion area, the webs between the apertures are curved in the longitudinal direction of the catheter. In a plan view of the tip, this results in a cross-shaped or star-shaped arrangement of the webs, depending on the number of apertures.

In one embodiment of the invention, the apertures have openings or are preferably formed completely by openings. The edges or boundaries of the apertures or openings are rounded or bevelled so as to provide a smooth transition of the adjoining surfaces. Inside it, the catheter head can have a channel which, together with a channel of the catheter, can form a drainage line in the proximal direction. The channel is connected to the openings that form the apertures. It is thus possible to use the openings as drainage openings for removal or delivery of fluid from or to the surrounding tissue. In order to form the drainage channel, a fastening piece suitable for fastening to a connecting pipe, preferably to a flexible tube part, of the catheter can adjoin the connection area in the longitudinal direction. The diameter of the connecting pipe or of the tube part on the fastening piece corresponds substantially to the diameter of the connection area, so as to give a smooth transition between these structural parts.

BRIEF DESCRIPTION OF THE FIGURES

An embodiment according to the present invention is shown in the drawings. Features of the measurement device that are evident from the figures are to be regarded as belonging to the scope of the disclosure and are not to be interpreted in any way as limiting the invention. In the drawings:

FIG. 6a shows a longitudinal section through a measurement device according to FIG. 1 along a first longitudinal plane;

FIG. 6b shows a longitudinal section through a measurement device according to FIG. 1 along a second longitudinal plane perpendicular to the first plane;

DETAILED DESCRIPTION

In the following description, the end with the catheter tip is designated as the distal end of the catheter probe, and the opposite end is designated as the proximal end.

Figure 1:
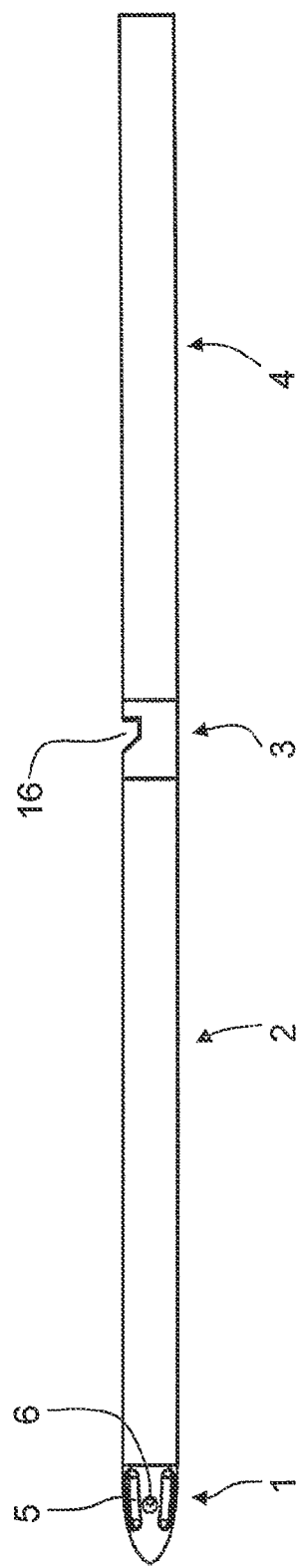
FIG. 1 shows an overall view of a measurement device according to the present invention.

FIG. 1 shows a measurement device according to the present invention which has a tip element 1 at a catheter head, a first connection tube 2, a middle piece 3, and a second connection tube 4. The first and second connection tubes 2, 4 are each preferably made from a flexible tube part. The text below therefore refers to a tube part, although this is also understood to mean other types of connection tubes 2, 4 that permit insertion of the catheter into the body tissue.

The tip element 1 is provided at a distal end of the measurement device. At the proximal end, the measurement device has a plug connector (not shown) or is guided directly into a processing unit for conversion and evaluation of the measurement signals. The tip element has several elongate openings 5, which form apertures in the surface of the catheter head. The openings 5 are provided for drainage of fluid in the surrounding tissue. Moreover, a round opening 6, in which a pressure sensor can be arranged, is provided between two elongate openings 5. However, the pressure sensor can also be arranged adjacent to, but not between, these irrigation openings 5. Electronic or optomechanical means, for example a silicon micromembrane, can be used as pressure sensors. The middle piece 3 has an indentation or aperture 16 into which a light conductor opens and through which light, delivered through the light conductor, can be emitted into the surrounding medium. The first tube part 2 can be varied in length depending on the intended nature of use of the measurement device.

Figure 2:
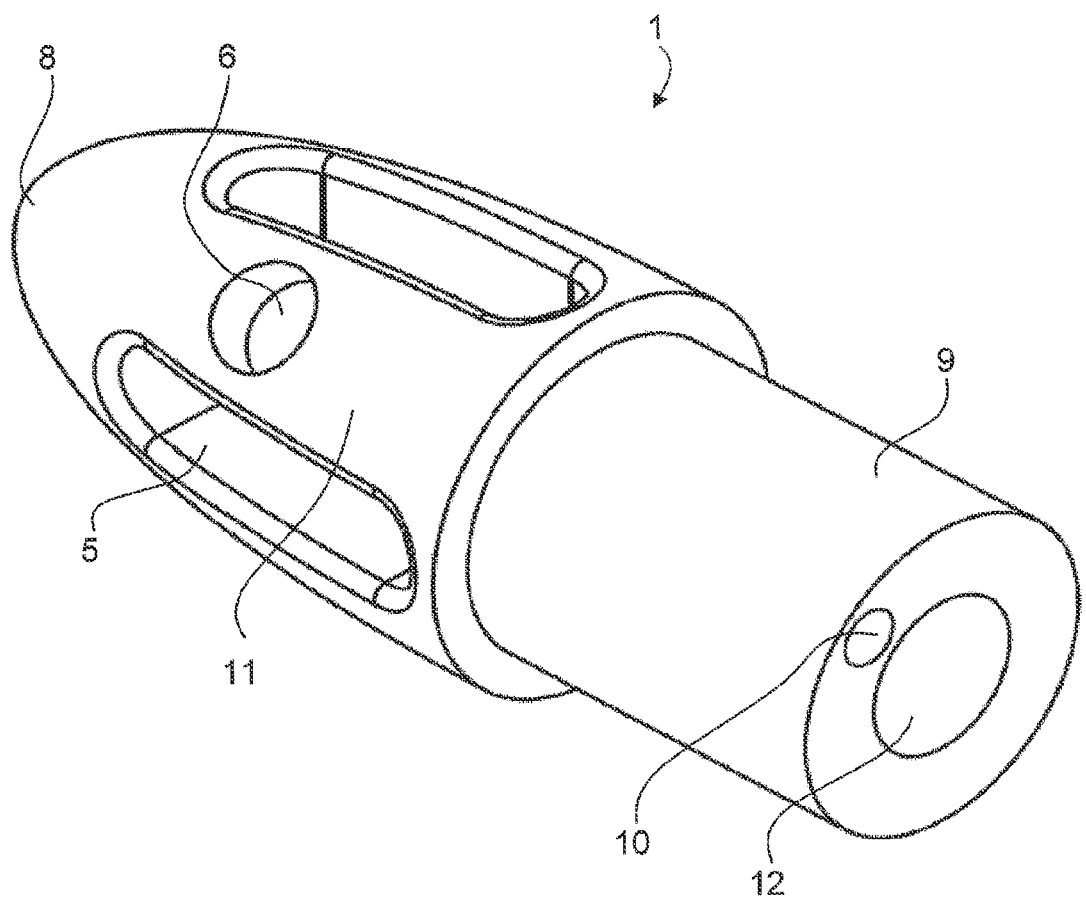
FIG. 2 shows a perspective view of a catheter head according to the present invention.

FIG. 2 shows a perspective view of the catheter head in the form of the tip element 1. The tip element can be made of plastic or of metal. The tip element is divided into a distal insertion area and an adjoining connection area. In the insertion area, the tip element has an oval, parabola-shaped or round tip 8. The insertion area has a diameter increasing from the tip 8 in the direction of the connection area. The tip 8 is closed at its center. The tip 8 is followed shortly thereafter by one or more elongate apertures or openings 5, which are arranged alongside one another in the circumferential direction. The embodiment shown in FIG. 2 has four openings, of which two can be seen in FIG. 2. Between the elongate openings 5, webs 11 are formed in the circumferential area and extend from the connection area into the tapering area of the tip 8 and are thus slightly curved. The edge areas of the elongate openings 5 are rounded or trimmed, so as to give a gentle transition from the circumferential surface of the catheter head to the edge areas of the openings 5. The slight curvature of the webs means that, in the tip area, they run towards the center or radially towards one another. The space between two adjacent elongate openings 5, which space forms the webs 11, is approximately as wide as the width of one elongate opening. Because of the slight curvature of the webs, the circumferential area tapers in the direction of the tip.

At the proximal end, the tip element 1 has a fastening piece 9, which is adjoined by the first tube part 2. The fastening piece 9 is part of the connection area or adjoins the latter. The fastening piece 9 is designed like a sleeve. A tubular structure can be placed with a form fit over the circumference of the fastening piece 9. In the circumferential wall of the fastening piece 9, a channel 10 extends in the longitudinal direction all the way from the distal end into the insertion area. The channel 10 serves for the passage of pressure measurement elements. For example, electrical or optical leads can be routed through the channel 10 as far as the opening 6, in which a pressure sensor can be arranged.

The elongate openings 5 serve for the drainage of the surrounding tissue. The drainage fluid is conveyed through an axially extending channel 12, which extends into the insertion area of the catheter head. It is an advantage of the present invention that the pressure sensor can be arranged between the elongate openings 5 and therefore carries out a pressure measurement at the same level in the surrounding tissue where a fluid can be discharged via the drainage opening.

If the tip and the middle piece are made of plastic, the tip preferably has an X-ray marking, so as to allow the positioning of the tip to be checked.

Figure 3:
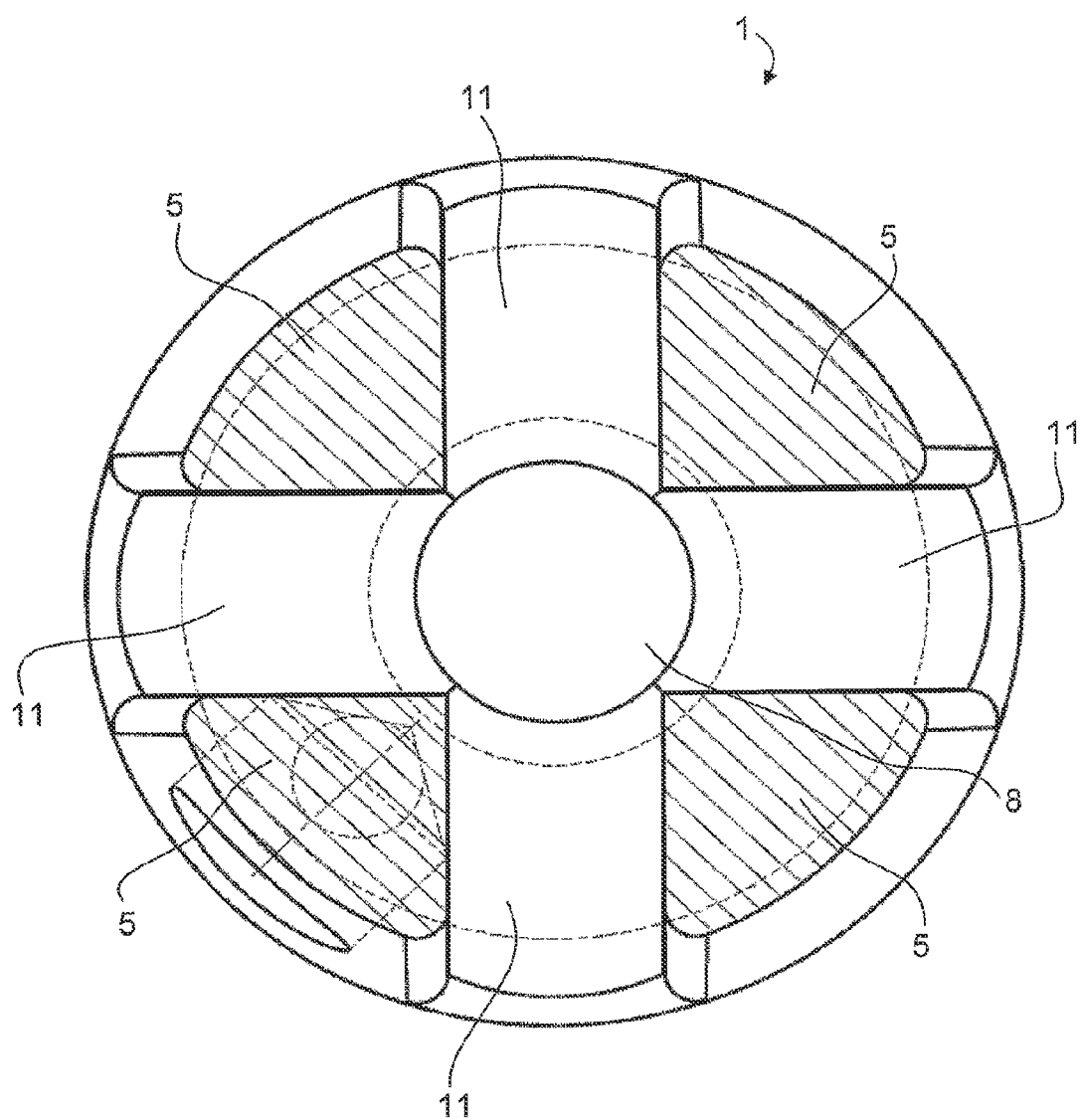
FIG. 3 shows a front view of the catheter head according to FIG. 2.

FIG. 3 shows a schematic front view of a tip element 1. At the center, the tip 8 can be seen as the frontmost curve of the catheter head. Arranged around this center are the four apertures in the form of elongate openings 5 which, in plan view, form a free space between each other. The circumferential areas between the elongate openings 5 form the webs 11, which extend from the center of the tip 8 to the outer circumference of the connection area and form a kind of guide structure for the tip element 1 upon insertion into a cerebral tissue. The webs 11 appear in a cross-shaped arrangement in the plan view in FIG. 3. When the catheter head is inserted into the tissue, the tip 8, whose diameter is smaller than the diameter of the overall tip element 1, and the surface of the webs 11 are pressed directly onto the tissue. At first, no pressure is applied to the tissue in the area of the apertures, that is to say in the area of the elongate openings 5. The tissue is gently braced and spread apart by the webs 11, such that the catheter head can penetrate into the tissue and, in doing so, causes minimal trauma. It is only after the tissue in the insertion area of the tip element 1 has been initially widened by the webs 11 that the tissue is spread open completely across the entire diameter of the connection area. By means of this design of the catheter head of the measurement device, it is possible to insert the measurement device into interior areas of the brain virtually without injury.

Figure 4:
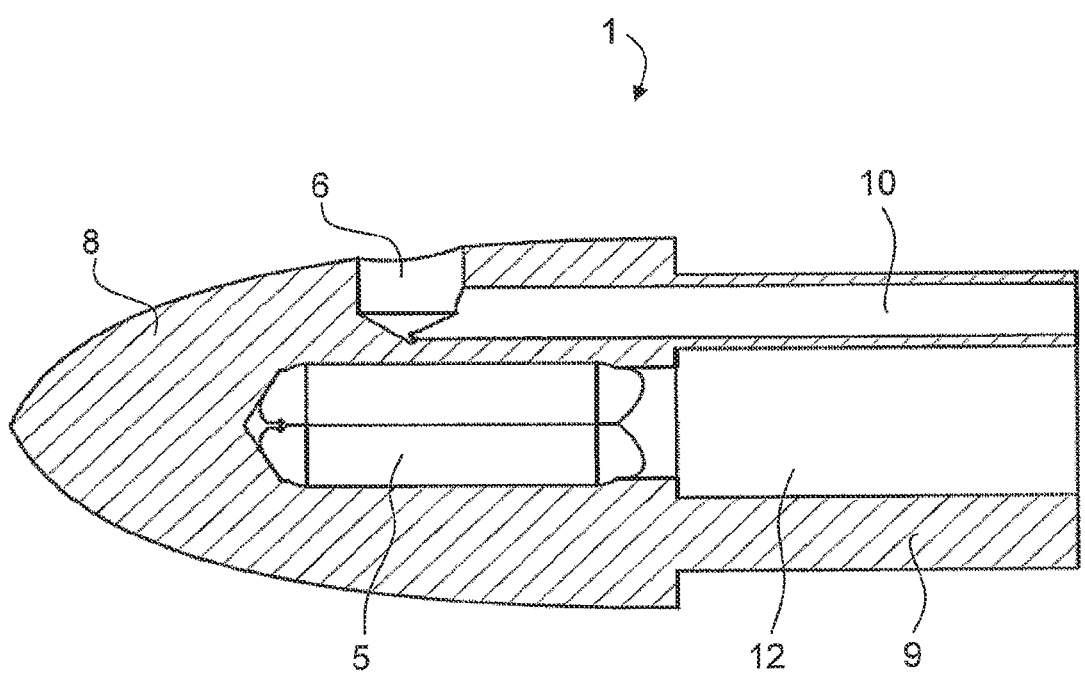
FIG. 4 shows a longitudinal section through the catheter head according to FIG. 3.

FIG. 4 shows a cross section along the longitudinal axis of a tip element 1. It can be seen that the tip element 1 in the insertion area and the tip 8 has a smaller diameter, which increases in the proximal direction as far as the connection area, which is adjoined by the fastening piece 9. The channel 10 extends in a straight line in the longitudinal direction as far as the opening 6, which is provided for a pressure sensor. In the interior, the four elongate openings 5 are adjoined by a guide channel 12, which is provided for removal of drainage fluid. In this view, the frontmost area of the tip 8 is shown as being pointed, which ensures that the widening of the tissue is optimized while no damage can be caused by scratching or cutting. The tip 8, or the cross section through the webs 11 of the catheter head, is substantially parabola-shaped.

Figure 17:
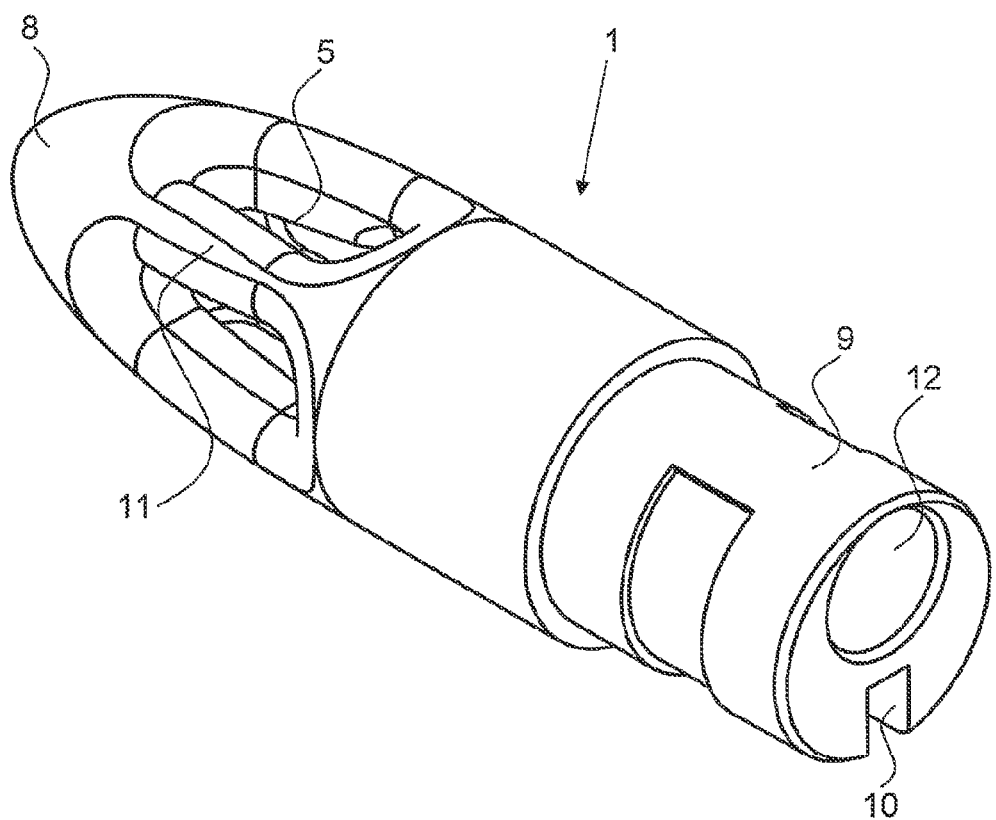
FIG. 17 shows a perspective view of a catheter head according to the present invention, in another embodiment.

FIG. 17 shows an embodiment of a tip element 1 in an alternative to FIG. 2. Identical parts are provided with identical reference signs. The tip 8 is once again rounded. The openings 5 lie closer to one another than in the embodiment according to FIG. 2, and they are separated from one another only by short webs 11. The webs preferably have a width that is a multiple smaller than the width of the individual openings. The drainage channel 12 extends axially offset in relation to the longitudinal center axis of the tip part 1. The pressure sensor channel 10, or the channel for other electrical lines, is in this case open. The pressure sensor is preferably arranged on that side of the openings 5 lying opposite the tip 8 or is located in the middle piece.

Figure 5:
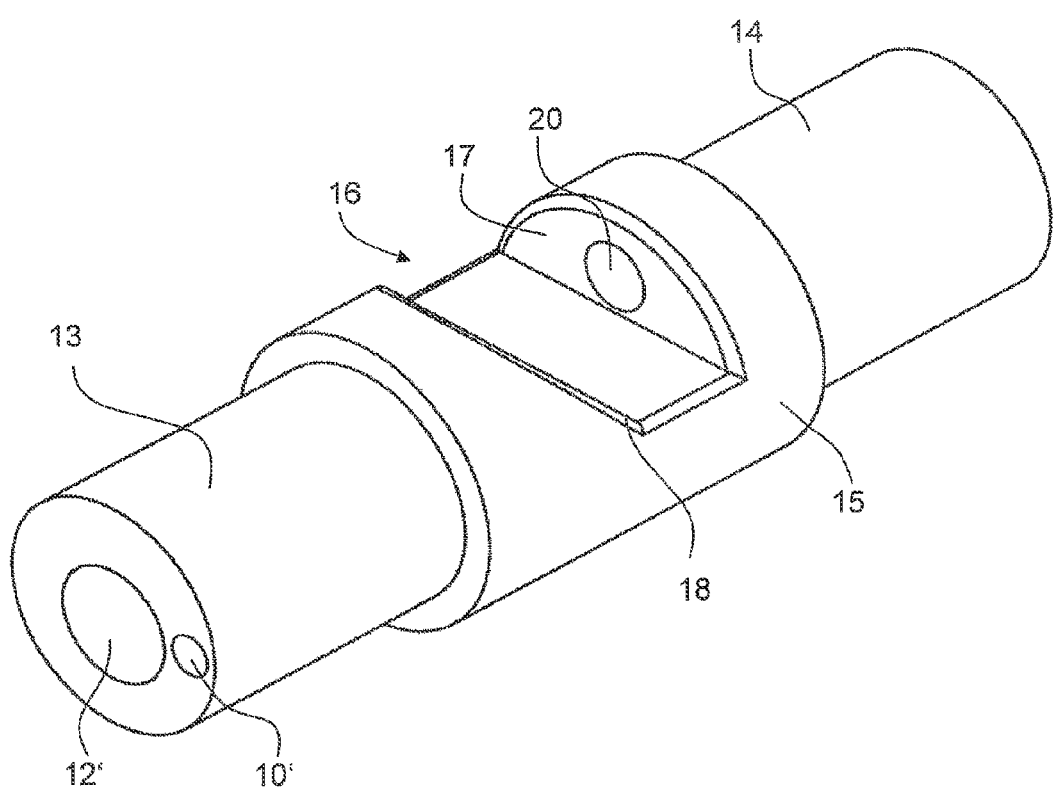
FIG. 5 shows a perspective view of a first embodiment of a middle piece of a measurement device according to the present invention.

FIG. 5 shows a middle piece 3 according to the present invention. The middle piece 3 has a distal fastening piece 13 and a proximal fastening piece 14. The fastening pieces 13 and 14 are similar to the fastening piece 9. They are sleeve-shaped and have a central passage for a drainage channel 12' for drainage of fluid and, in their circumferential wall, they have a continuous channel 10 for leads serving the pressure sensor in the tip element 1. The guide channel or drainage channel 12' in the middle piece 3 is analogous to the channel 12 in the tip element 1 and forms a continuation thereof On the middle piece 3, a middle area 15 is formed between the proximal fastening piece 13 and the proximal fastening piece 14. In the embodiment according to FIG. 5, the middle area 15 has a wedge-shaped indentation 16 which, instead of extending all the way to the drainage channel 12', leaves the latter closed. At its proximal end, the indentation 16 extends with a light exit surface 17, from which an optical conductor emerges, perpendicular to the longitudinal axis. At its distal end, the indentation 16 has a reflection surface 18, which preferably extends at a 45° angle to the longitudinal axis of the middle piece 3 and to the surface 17. A channel 20, which ends in the light exit surface 17 of the indentation 16, extends through the circumference of the distal fastening piece 14 and the proximal end of the middle piece 3, in the longitudinal direction of said middle piece 3. The opening of the channel 20 in the indentation 16 thus lies opposite the oblique surface 18. The channel 20 is provided for guiding a light conductor. The light conductor can also extend past the light exit surface and protrude into the indentation 16. The light from the light conductor strikes the opposite reflection surface 18. A mirror or other type of reflector, arranged on the reflection surface 18, reflects the light from the light conductor into the surrounding tissue around the middle piece 3. The reflector can be mounted as a separate element on the reflection surface 18, or the reflection surface 18 itself can be configured as a reflector surface. For example, a gold coating can be provided as reflection surface. It is also possible for the surface 18 or the reflector to have a slightly curved shape, such that the incident beam of light is widened slightly. The indentation 16 is filled with epoxy resin, such that the surface of the middle area 15 is cylindrical.

An individual optical fibre is preferably suitable as light conductor. There are preferably not more than five optical fibres present. Two or three fibres can likewise be used.

FIGS. 6a and 6b each show longitudinal sections through a first embodiment of a catheter probe according to the present invention, these longitudinal sections being offset by 90° to each other. FIG. 6a shows, from left to right, a tip element 1, a first tube part 2, a middle piece 3 and a second tube part 4 according to the view from FIG. 1. The first tube part 2 has one end pushed over the fastening piece 9 of the tip element 1 and has the other end pushed over the fastening piece 13 of the middle piece 3. In the interior of the first tube part, between the tip element 1 and the middle piece 3, there is another flexible tube 21 that interconnects the guide channels 12 and 12' of the tip element and of the middle piece. The channels 12 and 12' form, together with the tube 21, a drainage channel for fluid that is intended to be removed from the tissue surrounding the catheter tip, by way of the openings 5. The length of the tube parts 4 and 21 can be varied, such that the position of the middle part 3 in the tissue can also be adjusted, i.e. tube parts of different lengths can be fitted between the tip element and the middle piece.

The wedge-shaped indentation 16 with the light exit surface 17 and the reflection surface 18 can be seen on the middle piece 3. The channel 20 opens into the light exit surface 17. The light exit surface 17 extends substantially perpendicular to the longitudinal axis of the catheter, although it could also be arranged at an angle thereto. An optical conductor, guided through the channel 20, is guided onwards through the second tube part 4 to a light source (not shown).

A temperature measurement channel 22 is also provided in the circumferential wall of the middle piece 3, on the proximal side, the temperature measurement channel 22 beginning on the side of the second tube part 4 and ending roughly at the center of the middle piece 3. The temperature measurement channel 22 is provided for a temperature sensor that measures the temperature of the surrounding tissue. The temperature sensor is arranged at this point near the outer periphery of the catheter and is able to measure the temperature in the tissue without impediment or distortion. Leads (not shown) run from the temperature sensor through the second tube part 4 to the processing unit and transmit a temperature signal to the processing unit.

FIG. 6b shows, within the tip element 1, the pressure sensor channel 10 which extends from the proximal end of the tip element 1 as far as the opening 6. In the opening 6, there is a pressure sensor whose leads run through the channel 10 and the space between the first tube part 2 and the inner tube 21 as far as a channel 10' in the middle piece 3. At the proximal end of the middle piece, the leads emerge from the channel 10' and are routed further through the second tube part 4 as far as the processing unit, to which they transmit a signal corresponding to the pressure in the medium surrounding the tip element 1 or in the guide channel 12. The processing unit is able to control the drainage of fluid through the drainage channel depending on the pressure signal from the pressure sensor. Manual drainage can also be performed.

The channel 12' on the middle piece 3 is widened conically at its distal end. This funnel-shaped opening facilitates insertion of a guide wire, which is used to guide the catheter probe during insertion into the body tissue.

The optical light conductor and the leads for the pressure sensor and temperature sensor can be routed freely within the interior of the second tube part 4. However, an inner tube can also be provided in this tube part, such that the leads are routed through the space between the outer tube and inner tube. The second tube part 4 can be adjoined by a plug in which the leads end. The plug can be fitted directly to the processing unit or to another plug, which in turn leads to the processing unit.

When examining a body tissue, for example the cerebral tissue in the interior of the brain, an opening is made in the cranium. A holder for the catheter is provided over the opening and holds the catheter as far as possible perpendicular to the surface of the head during insertion and also in the inserted state. Thus, the holder on the one hand covers the opening in the head and on the other hand ensures that the catheter is not accidentally deflected from its intended path during its insertion and during measurements. In this way, it is possible to avoid contamination of the area being examined and to avoid unnecessary damage to the surrounding tissue.

The catheter probe is inserted carefully through the tissue as far as a desired measurement position, for example until it rests on the floor of a ventricle. The inventive design of the catheter head means that in doing so there is only a minimal impact on the cerebral tissue, such that the tissue is not unnecessarily damaged and the measurement is not distorted.

To measure the flow of blood through the cerebral tissue, light in the near infrared range is conveyed through the light conductor in the channel 20 to the reflection surface 18. The light source can, for example, also be provided on the processing unit itself. The beam of light directed onto the surface 18 is reflected there and sent out into the cerebral tissue. There, it is absorbed and reflected among other things on the oxygenated and deoxygenated hemoglobin and, if appropriate, on the indocyanine green. Some of the reflected light falls back onto the reflection surface 18, and as a result is fed into the light conductor in the channel 20 by reflection on the surface 18. The channel guides the reflected light back to the processing unit, in which it is evaluated by, for example, an analog/digital converter. At the same time, the temperature in the measured tissue can be determined by the temperature sensor in the channel 22, and the pressure in the area surrounding the tip of the probe can be determined by the pressure sensor. If necessary, drainage can be performed immediately via the channel 12, 12'.

By means of the measurement probe being guided by the holder, the probe can be turned in its measurement position without thereby being deflected and damaging the surrounding tissue. By turning the probe, the measurement range in the tissue can be greatly widened. It is possible to cover a measurement field that extends through 360° around the middle piece 3. The tube parts between the tip and the middle piece can be flexible or rigid.

Figure 7:
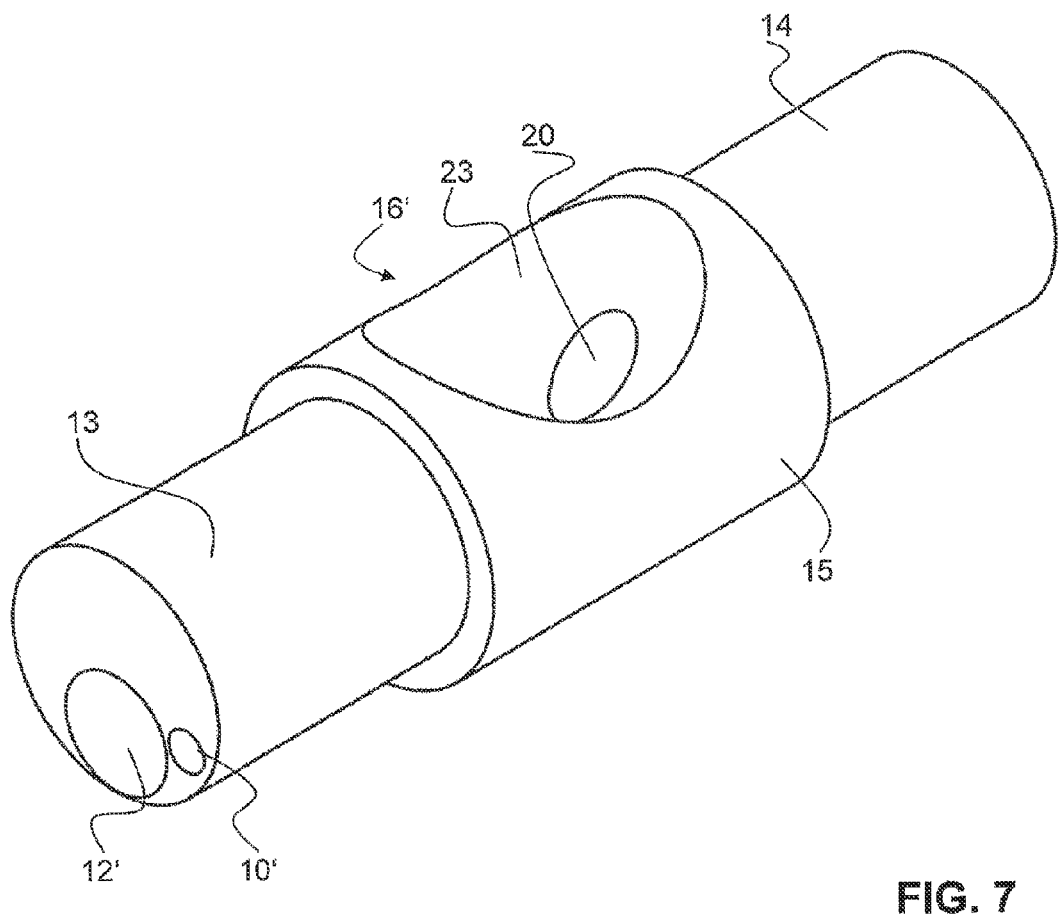
FIG. 7 shows a perspective view of a second embodiment of a middle piece of a measurement device according to the present invention.

FIG. 7 shows a second embodiment of a middle piece according to the present invention. In this design of the middle piece, the drainage channel 12' is eccentric to the longitudinal axis. In this way, the middle piece can be constructed with a smaller diameter. Moreover, the recess according to the invention is provided here in the form of an aperture 16' which is sunk in a curved or rounded shape into the middle piece. An inner surface 23 thus formed comprises a light exit surface area at the proximal area, and, lying opposite this at the distal area, it has a reflection surface area. In terms of its function, the light exit surface area corresponds to the light exit surface 17 from the embodiment according to FIGS. 1 to 6, and the reflection surface area accordingly corresponds in terms of its function to the reflection surface 18. The light-conducting channel 20 opens out from the light exit surface area. Light emitted from an optical conductor in the light-conducting channel 20 strikes the opposite reflection surface area, from which it is reflected into the surrounding tissue. The curvature of the aperture 16' is designed such that light reflected from the tissue is focussed into the optical conductor.

Figure 8:
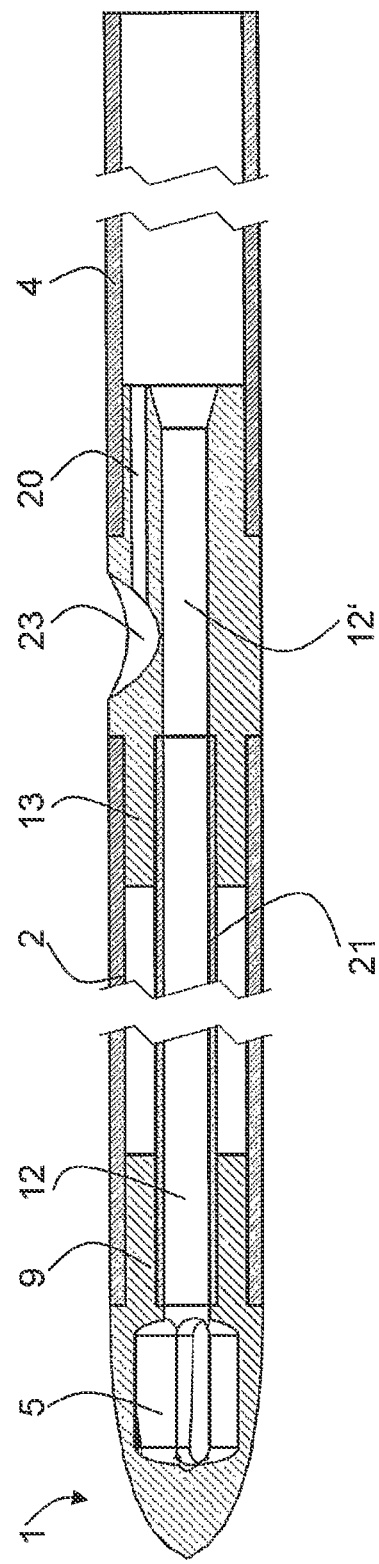
FIG. 8 shows a longitudinal section through a measurement device from FIG. 1 according to the second embodiment.

FIG. 8 shows a longitudinal section through a measurement device with a middle piece according to FIG. 7, but the drainage channel 12' is arranged in a central position here. The aperture 16' reaches almost as far as the drainage channel 12' but leaves the latter closed. The curvature or roundness of the aperture 16' is such that light from the channel 20 is oriented directly onto the focal point. The other elements of the measurement device in this embodiment correspond to those from FIGS. 6a and 6b.

Figure 9:
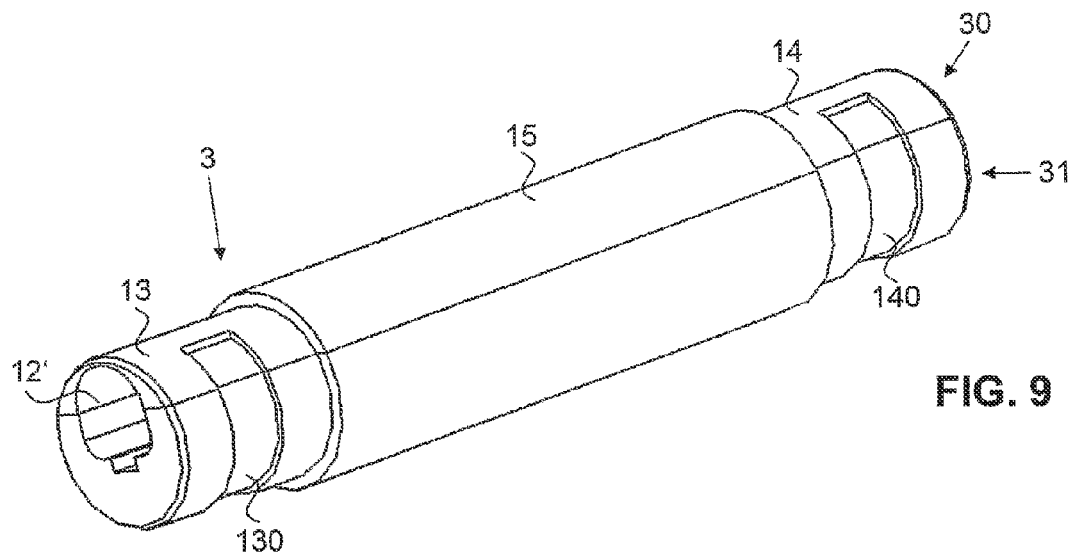
FIG. 9 shows a perspective view of a middle piece according to the invention.
Figure 10:
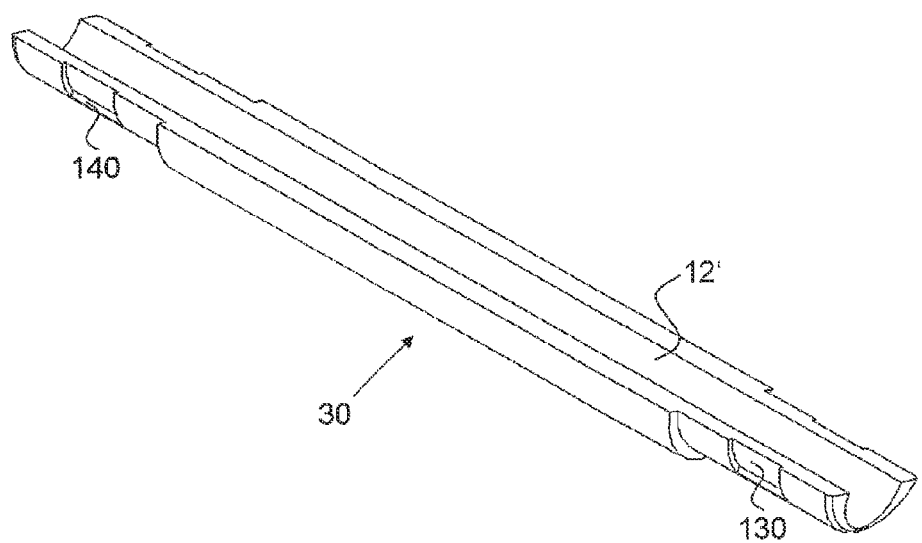
FIG. 10 shows a perspective view of a lid of the middle piece according to FIG. 9.

FIGS. 9 to 15 show the middle part 3 according to the invention in a preferred embodiment. Identical parts are provided with the same reference signs as in the above examples. The middle part 3 is made of plastic and is preferably produced by injection moulding. It is composed of at least two parts, namely a lower part 31 and a lid 30. Both are configured as half tubes, as can be seen in FIG. 10 for the lid 30. Together they form a tubing with a middle area 15, a distal fastening piece 13 and a proximal fastening piece 14. Grooves 130, 140 are provided extending radially about the circumference of the two fastening pieces 13, 14 in order to permit a connection to adjoining tubes. These grooves serve as adhesive grooves for a form fit and force fit. An equivalent groove can be seen in FIG. 17.

Instead of flexible tubes, rigid connector parts can also be present on both sides or on one side.

In contrast to the above examples, the recess in which the mirror, the fibre end and any measuring means are arranged is now covered by the lid 30. The lid 30 can be connected to the lower part with a form fit and/or a force fit and/or a materially cohesive fit.

Lid 30 and lower part 31 are preferably made from the same material. At least the lid 30, however, must be made from a material that is transparent for the optical wavelength used. They are preferably made of polyamide or polycarbonate.

As can be seen from FIG. 9, the lower part 31 and the lid 30 form a common inner drainage channel 12' with a cable channel 120. The drainage line already described above and any measurement lines extend through this drainage channel 12' as far as the distal head part of the catheter.

Figure 11:
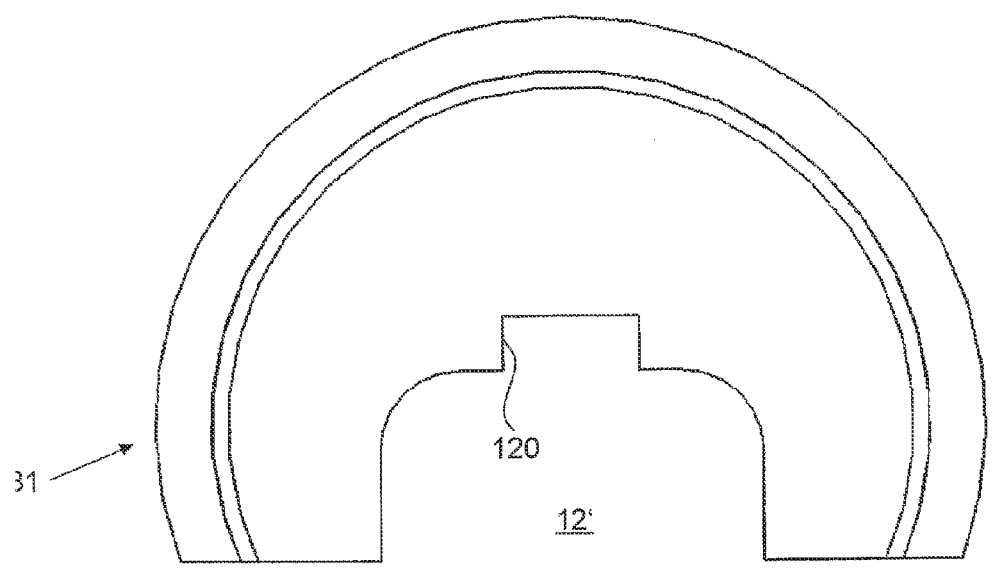
FIG. 11 shows a view of the distal end of a lower part according to FIG. 9.
Figure 12:
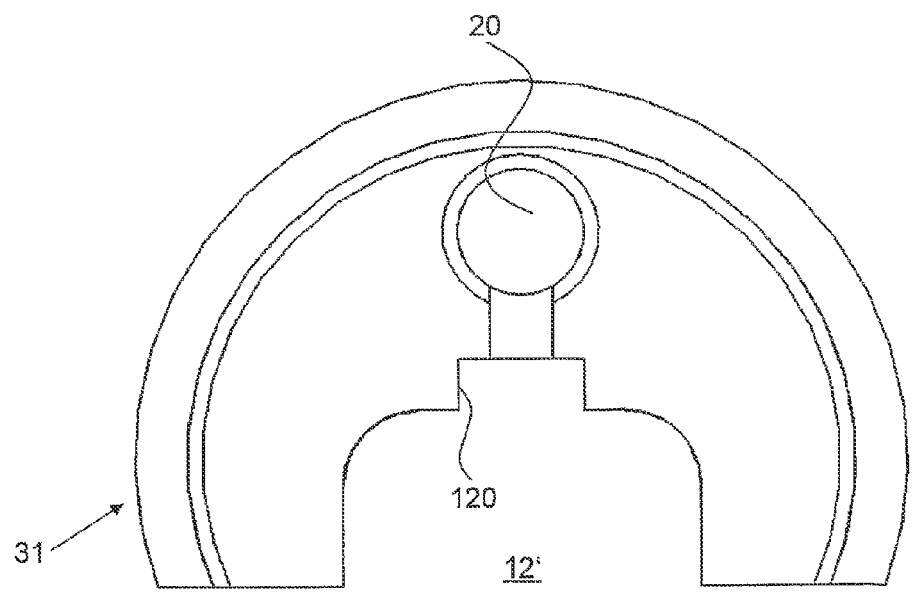
FIG. 12 shows a view of the proximal end of the lower part of the middle piece according to FIG. 9.

FIG. 11 shows the distal end of the middle part 3 with the drainage channel 12'. FIG. 12 shows the inner proximal end of the middle part 3 not visible in FIG. 9. A light conductor channel 20 extends parallel to the drainage channel 12' but spaced apart therefrom. Here too, it is preferable to use exactly one optical fibre as light conductor. However, there can also be up to five optical fibres, in particular two or three.

Under the aperture 16, the drainage channel 12' extends along the entire length of the middle piece 3.

Figure 13:
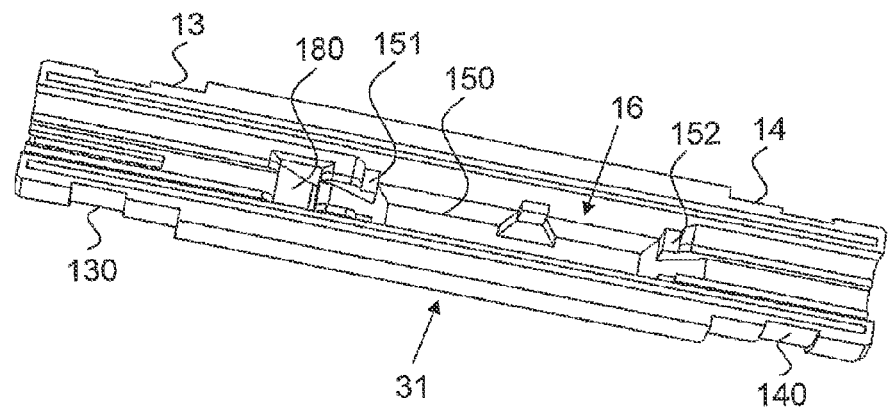
FIG. 13 shows a perspective view of the lower part according to FIG. 12.
Figure 14:
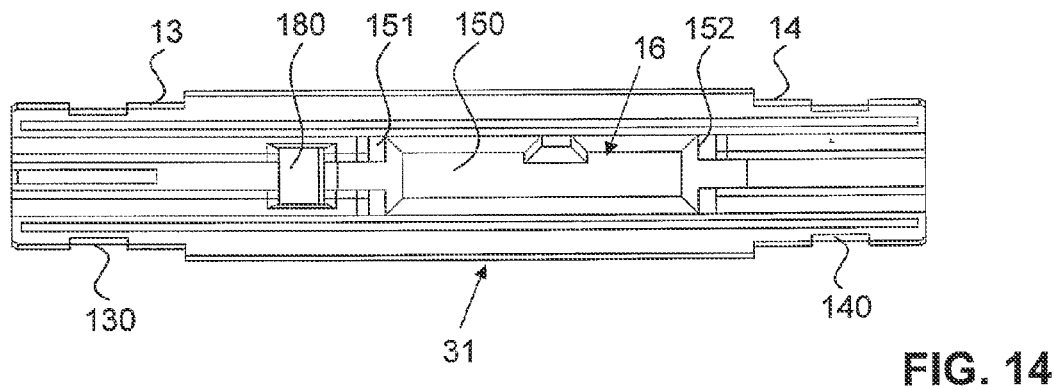
FIG. 14 shows a top view of the lower part according to FIG. 12.
Figure 15:
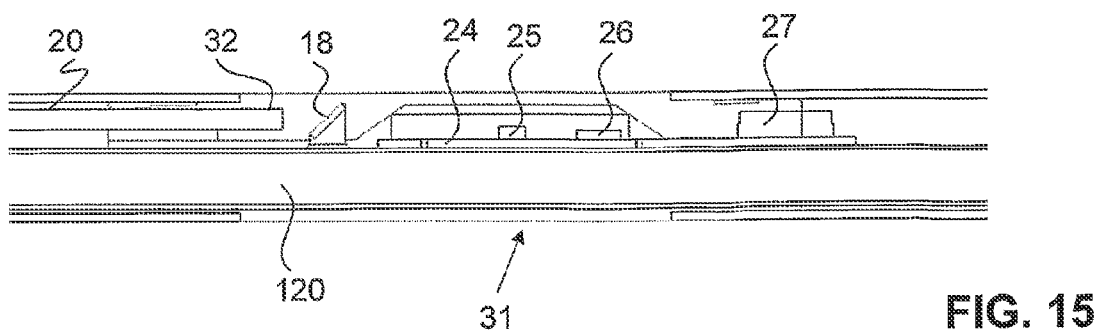
FIG. 15 shows a longitudinal section through the lower part according to FIG. 12 with optical conductor and circuit board.

FIGS. 13 to 15 show the lower part 31 in detail. It has the aperture 16. A receiving area 150 for the electronics is present in this aperture 16. Proximal and distal receiving surfaces 151, 152 are formed integrally on both end areas of the receiving area 150. A circuit board 24 can be secured, for example adhesively affixed or screwed, onto these plane receiving surfaces 151, 152.

A photodetector 25 can be secured on the circuit board 24. It is also possible for a temperature sensor 26 and/or a pressure sensor 27 to be present. However, these sensors can also be arranged at another location. As has already been mentioned above with reference to the other examples, the pressure sensor is preferably arranged in the tip element 1.

An inclined surface 180 is present outside this receiving area 150. This inclined surface 180 can itself be designed as a reflection surface. However, it preferably serves as a holder for a mirror 18. The mirror 18 in this example is a plane-parallel mirror, such that the inclined surface 180 is also designed as a plane surface. The inclined surface 180 is preferably oriented at a 45° angle to the longitudinal direction of the middle piece 3.

The light conductor channel 20 extends in the lower part 31 and ends adjacent to the inclined surface 180. The light conductor 32 is shown in FIG. 15. It will be seen that it ends before the mirror 18, such that light emitted from the light conductor 32 is deflected from the mirror 18 and conveyed radially outward.

In this example, light reflected in the tissue is no longer fed back via the light conductor and evaluated. It is instead detected by the photodetector, and an electrical signal is transferred to an external evaluation unit via a signal line. The cables necessary for this purpose run inside the cable channel 120.

This middle part 3 can be used with one of the tip elements 1 described above. However, it can also be used with other tip elements 1.

Figure 16:
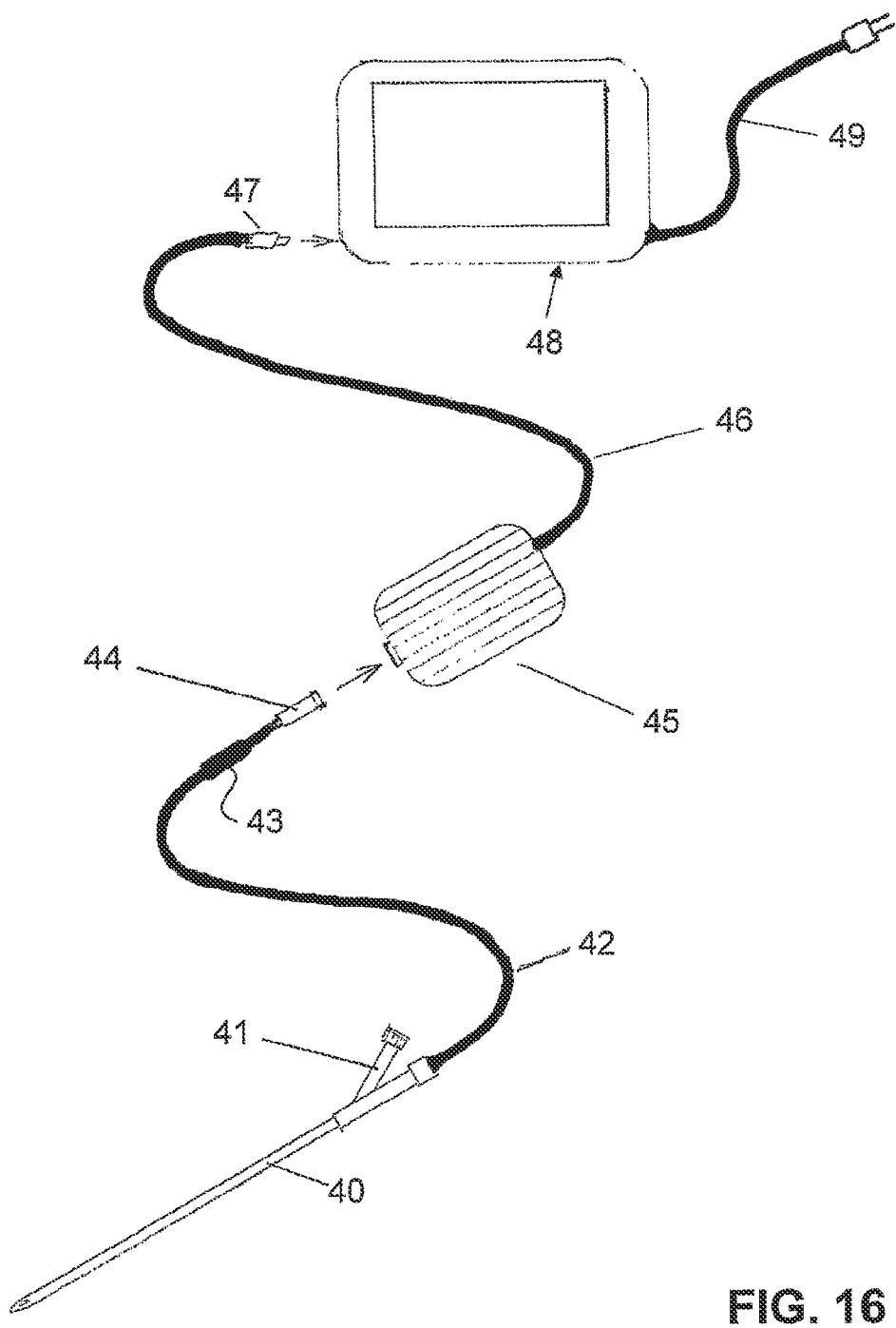
FIG. 16 shows a schematic view of the measurement device according to the invention.

FIG. 16 shows the overall system. The catheter or the probe 40 is provided at the end of the drainage channel with a Luer lock 41. A first line 42, which comprises electrical conductors and also at least one optical conductor, is connected with a distal end to the probe 40. In the area of the proximal end, it has a calibration unit 43, and it is provided at this end with a first plug 44. This plug 44 permits a connection to a portable electronics unit 45. This electronics unit 45 preferably comprises a potential insulator, an A/D converter, a pre-amplifier, and a light source for coupling light into the optical conductor that leads to the middle part 3 of the catheter.

The portable electronics unit 45 is connected to an evaluation unit 48 via a second, purely electrical line 46, which in turn is provided with a second plug 47. A third line 49 represents the main supply cable. However, the evaluation unit 48 can of course also be battery-operated.

The advantage of this overall system is that the electronics unit 45 is relatively close to the patient. The sensitive optical lines can therefore be made relatively short.

In the examples described above, an optical glass fibre is preferably used in the near infrared range. Its diameter is preferably approximately 0.6 mm inclusive of its sheath and approximately 0.2 mm without its sheath. The length of the middle piece 3 is preferably 20 to 30 mm, and its diameter is preferably 3 mm. The mirror surface preferably measures 1×1 mm. The drainage channel preferably has a diameter of 0.9 to 1.5 mm, preferably 1.0 or 1.2 mm. The width of the circuit board is preferably 1.4 mm. A 9-pole or 10-pole cable, which extends as far as the plug 44, is normally used inside the middle piece 3.

The invention claimed is:

1. A device for measuring the flow of blood through a body tissue, comprising:
    a catheter with a catheter head for insertion into the interior of a body tissue;
    an optical conductor inside the catheter;
    a light source for emitting a beam of light into the body tissue by means of the optical conductor; and
    a processing unit for determining the rate of blood flow by means of a beam of light reflected from the body tissue;
    wherein the catheter has a middle piece with a recess comprising a light exit surface area, from which the optical conductor emerges, and a reflection surface area which lies opposite the light exit surface area and which is oriented at least partially obliquely with respect to the longitudinal axis of the optical conductor;
    the optical conductor being arranged in such a way that a beam of light emitted from the light source is directed to the reflection surface area, the emitted beam of light can be deflected on the reflection surface area and can be reflected into the surrounding body tissue; and
    wherein the distance between the catheter head and the middle piece is varied using connection elements of different lengths.

2. The device of claim 1 wherein the reflection surface area and the optical conductor are arranged in such a way that a beam of light reflected on the body tissue can be reflected on the reflection surface area and fed into the optical conductor.

3. The device of claim 1 wherein at least one photodetector is arranged in the middle piece and light reflected on the body tissue can be detected by the at least one photodetector.

4. The device of claim 3 wherein a circuit board is present in the recess and wherein the at least one photodetector is arranged on the circuit board.

5. The device of claim 1 wherein the reflection surface area is a mirror.

6. The device of claim 5 wherein the middle piece has an inclined surface on which a mirror is secured, wherein the mirror forms the light reflection surface area.

7. The device of claim 1 wherein the middle piece is rigid.

8. The device of claim 1 wherein the connection elements comprise a first connection tube and wherein the device further comprises a second connection tube, wherein the middle piece has a distal fastening piece for fastening to the first connection tube and a proximal fastening piece for fastening to the second connection tube.

9. The device of claim 8 wherein the catheter head is rigid, and wherein the catheter head has a third fastening piece for fastening to the first connection tube, such that the head part is arranged at a distance from the middle piece.

10. The device of claim 8 wherein at least the first connection tube is flexible.

11. The device of claim 1 wherein the middle piece is made of metal or plastic.

12. The device of claim 1 wherein a pressure sensor and/or a temperature sensor are arranged in the middle piece.

13. The device of claim 1 wherein the middle piece comprises a lower part and a lid, the lower part and the lid being configured as half tubes and together forming a tubing.

14. The device of claim 13 wherein the lid covers the recess.

15. The device of claim 14 wherein the lid is made of a material transparent to the emitted light.

16. The device of claim 1 wherein the recess is filled with a filler material transparent to light, wherein an outer surface of the filler material forms a smooth transition to a circumferential surface of a surrounding area of the middle piece.

17. The device of claim 1 further comprising a drainage channel extending through the middle piece.

* * * * *